(12) United States Patent
Butera (10) Patent No.: US 9,421,095 B2
(45) Date of Patent: Aug. 23, 2016

(54) VALVE PROSTHESIS FOR IMPLANTATION IN BODY CHANNELS

(75) Inventor: Gianfranco Butera, San Donato Milanese (IT)

(73) Assignee: GENOMNIA SRL, Milan (IT)

( * ) Notice: Subject to any disclaimer, the term of this patent is extended or adjusted under 35 U.S.C. 154(b) by 0 days.

(21) Appl. No.: 12/411,870

(22) Filed: Mar. 26, 2009

(65) Prior Publication Data

US 2009/0254176 A1    Oct. 8, 2009

(30) Foreign Application Priority Data

Mar. 27, 2008    (EP) .................................. 08425200

(51) Int. Cl.
*A61F 2/24*    (2006.01)

(52) U.S. Cl.
CPC ............. *A61F 2/2418* (2013.01); *A61F 2/2403* (2013.01); *A61F 2/2412* (2013.01); *A61F 2/2415* (2013.01); *A61F 2/2475* (2013.01); *A61F 2230/0054* (2013.01); *A61F 2230/0067* (2013.01); *A61F 2250/0082* (2013.01)

(58) Field of Classification Search
CPC ........ A61F 2/24; A61F 2/2418; A61F 2/2475
USPC ............. 623/1.24, 2.14, 2.17, 2.18, 2.11, 2.1, 623/2.12
See application file for complete search history.

(56) References Cited

U.S. PATENT DOCUMENTS

| 3,714,671 | A | * | 2/1973 | Edwards et al. ............. 623/2.19 |
| 4,778,461 | A | * | 10/1988 | Pietsch et al. ................ 623/2.19 |
| 5,358,518 | A | | 10/1994 | Camilli |
| 6,299,637 | B1 | * | 10/2001 | Shaolian et al. ............. 623/1.24 |
| 6,503,272 | B2 | | 1/2003 | Duerig |
| 6,602,286 | B1 | * | 8/2003 | Strecker ....................... 623/1.24 |
| 7,267,686 | B2 | | 9/2007 | DiMatteo |
| 2001/0007083 | A1 | * | 7/2001 | Roorda ......................... 623/1.15 |
| 2001/0039450 | A1 | * | 11/2001 | Pavcnik et al. .............. 623/1.24 |
| 2002/0138135 | A1 | * | 9/2002 | Duerig .................. A61F 2/2418 623/1.24 |
| 2003/0055492 | A1 | * | 3/2003 | Shaolian et al. ............. 623/1.24 |
| 2003/0130729 | A1 | * | 7/2003 | Paniagua et al. ............. 623/2.11 |
| 2003/0209835 | A1 | * | 11/2003 | Chun .................... A61F 2/2412 264/339 |
| 2004/0260389 | A1 | * | 12/2004 | Case et al. .................... 623/1.24 |
| 2006/0265053 | A1 | * | 11/2006 | Hunt ............................ 623/1.24 |
| 2006/0282157 | A1 | | 12/2006 | Hill et al. |
| 2007/0100435 | A1 | * | 5/2007 | Case et al. .................... 623/1.24 |
| 2007/0288086 | A1 | * | 12/2007 | Kalmann ............. A61F 2/2418 623/1.24 |
| 2009/0132037 | A1 | * | 5/2009 | Hoffman et al. ............. 623/2.38 |

FOREIGN PATENT DOCUMENTS

| EP | 0667133 B1 | 1/2001 |
| EP | 0856300 B1 | 12/2004 |

(Continued)

*Primary Examiner* — Jacqueline Woznicki
(74) *Attorney, Agent, or Firm* — Lucas & Mercanti, LLP (57) ABSTRACT

The present invention regards a valve prosthesis (1; 40; 50; 60) comprising a stent (2) and characterized in that it comprises a valve (3) arranged in said stent (2) and bound thereto in at least one pre-established zone so that it can be deformed between a closed state in which said valve (3) is fully spread out in the stent (2), thus blocking the passage of a body fluid, and an open state in which said valve (3), due to the pressure of said body fluid, is substantially collapsed on an inner wall of said stent (2), thus permitting the flow of said body fluid. The invention also regards a method for making said valve prosthesis.

17 Claims, 10 Drawing Sheets

(56) References Cited

FOREIGN PATENT DOCUMENTS

| EP | 2019652 | B1 | 7/2010 |
|----|---------|----|--------|
| WO | 2005013857 | A | 2/2005 |
| WO | 2006/009690 | A1 | 1/2006 |
| WO | 2007/097983 | A2 | 8/2007 |
| WO | 2007139677 | A | 12/2007 |
| WO | 2008/140466 | A1 | 11/2008 |

\* cited by examiner

VALVE PROSTHESIS FOR IMPLANTATION IN BODY CHANNELS

CROSS-REFERENCE TO RELATED APPLICATIONS

This application claims the benefit of priority from European Paten Application No. 08425200.6, filed Mar. 27, 2008, the contents of which are incorporated herein by reference.

FIELD OF APPLICATION

In its most general aspect, the present invention refers to a valve prosthesis for implantation in body ducts.

In particular, the present invention refers to a valve prosthesis for the percutaneous substitution of an absent or non-functioning pulmonary valve, and a related method for making said valve prosthesis.

PRIOR ART

As known, the presence of a chronic pulmonary valve insufficiency, of size varying from slight to severe, represents a very common condition in patients treated for Tetralogy of Fallot in childhood.

A prevailing stenosis condition or steno-insufficiency condition can instead be created not only in patients with Tetralogy of Fallot, but also in patients with other pathologies of the right heart. Such anomalies can be created both in patients treated with duct between right ventricle and pulmonary artery and in patients in whom a prosthesis structure has not been implanted.

Chronic pulmonary insufficiency, stenosis and/or steno-insufficiency lead to a chronic overload of the right ventricle (diastolic or systo-diastolic according to the pathological conditions).

In the follow-up, these subjects can have right cardiac insufficiency, arrhythmia, and sudden death.

It should be noted that numerous patients operated on in pediatric age reach adult age and the number of these subjects with residue insufficiency, stenosis, or steno-insufficiency is progressively increased.

In order to correct such pathologies, the implantation is necessary of a valve prosthesis of biological or synthetic origin, which carries out the role of the absent or non-functioning natural valve.

If the patient is of pediatric age, it is not possible to implant synthetic prostheses, since the body growth would oblige the substitution of such implants after a short time period. Usually in such cases, implants known as xenografts or homografts are employed, though these tend to degenerate over time, since they are materials of biological origin.

The technique called Turrentine is also known ((1) Brown J W, Ruzmetov M, Vijay P, Rodefield M D, Turrentine M W. Right ventricular outflow tract reconstruction with a polytetrafluoroethylene monocusp valve: a twelve-year experience. J Thorac Cardiovasc Surg 2007; 133:1336-43. (2) Turrentine M W, McCarthy R P, Vijay P, McConnell K W, Brown Jw. PTFE monocusp reconstruction of the right ventricular outflow tract. Ann Thorac Surg 2002; 73:871-9. (3) Turrentine M W, McCarthy R P, Vijay P, Fiore A C, Brown J W. Polytetrafluoroethylene monocusp valve technique for right ventricular outflow tract reconstruction. Ann Thorac Surg 2002; 74:2202-05. (4) Maluf M A, Braile D M, Silva C et al. Reconstruction of the pulmonary valve and outflow tract with bicuspid prosthesis in tetralogy of Fallow. Ann Thorac Surg 2000; 70:1911-7), which provides for the implant of a sheet of ePTFE (expanded polytetrafluoroethylene) preformed in a suitable manner by the surgeon, who sutures it to the wall of the artery in such a manner that it carries out the function of a monocusp valve.

Although the ePTFE is not subject to wear, the application of such sheet is not an easy operation, since it requires an open heart operation in extracorporeal circulation. In addition, cases are known of patients who required multiple valve substitution procedures, and thus a plurality of extracorporeal circulation operations.

Moreover, there are devices known with the term "stent". A stent is composed of a biocompatible material lattice, capable of enlarging the transverse surface of blood vessels. The stent is normally percutaneously inserted inside the blood vessels by means of known angioplasty techniques. By means of such techniques, the stent is compressed around a known angioplasty balloon. The stent and the angioplasty balloon are integrally transported, inside the blood vessels, along a previously inserted guide. Once the final position has been reached, the angioplasty balloon is inflated, so to make the stent expand until it adheres to the walls of the blood vessel. At this point, the angioplasty balloon is deflated and brought outside, while the stent remains adhering to the walls of the blood vessel, pushing outward and therefore tending to maintain the blood vessel open. Nevertheless, due to recoil forces that the blood vessel imposes on the stent when the balloon is deflated, the cross section of the blood vessel tends to be reduced, thus decreasing the effectiveness of the stent.

The possibility to implant a xenograft is also known; this is a bovine jugular vein with its valve, sutured in a nitinol stent expandable with an angioplasty balloon. Such an approach, however, is not free of drawbacks: since this is a material of biological origin, it is therefore subject to degradation; the costs are high; the implant system has large diameter and therefore is considerably invasive, so that it can be used only in adolescent and adult patients.

The technical problem underlying the present invention is that of providing a valve prosthesis that can be percutaneously implanted which overcomes the abovementioned drawbacks of the prior art, in particular a valve prosthesis for use in cases of valve pathology in general and pulmonary pathology in particular that is easy to use, is less invasive and is capable of resisting the recoil forces of the destination blood vessels.

SUMMARY OF THE INVENTION

Such a technical problem is solved according to the invention by a valve prosthesis comprising a stent and characterised in that it comprises a valve arranged in said stent and bound thereto in at least one pre-established zone, so that it can be deformed between a closed state in which said valve is fully spread out in the stent, thus blocking the passage of a body fluid, and an open state in which the valve, due to the pressure of said body fluid, is substantially collapsed on an inner wall of said stent, thus permitting the flow of said body fluid.

DETAILED DESCRIPTION

The valve has a structure comprising a valve tissue compatible with the human body and blood, the tissue having a suitable softness and resistance so that it can be deformed from a closed state to an open state in order to permit the body fluid, in particular blood, to exert a pressure on this valve structure.

In particular, the valve structure composing the valve forms a continuous surface and is bound to the stent in pre-established zones, so to provide, by means of the stent, a suitable support for the valve in said zones, and at the same time inducing the valve structure to follow a pre-defined movement between an open state and a closed state under the changes of the blood pressure during cardiac activity.

In addition, the bond with the rigid stent advantageously avoids the displacement of the valve and thus any significant reflux event.

Preferably, the valve structure has a monocusp sail-like form in its fully spread out state, with substantially triangular longitudinal section and with rounded corners. A prosthesis according to the invention which incorporates one such valve structure is particularly adapted for use as pulmonary valve, for example in substitution of a malfunctioning native valve.

In such case, the wider end of the monocusp sail-like form, i.e. the base in the fully spread out state of the valve, is preferably positioned towards the distal part (pulmonary branches).

Moreover, preferably, the valve structure has a concave surface with curvature turned towards the distal part (pulmonary branches). This form advantageously produces an efficient structure in view of the systo-diastolic movement of the valve tissue.

In accordance with one embodiment of the invention, the valve is arranged tilted with reference to the longitudinal axis of the stent by an acute angle with respect to such axis preferably comprised in the range of 35°-50°.

In the case of a valve of monocusp sail-like form, a slope of the valve structure between the base and the apex of the valve itself forming an angle of about 45° with the longitudinal axis of the stent permits initiating and completing the closure of the valve structure itself. In particular, this slope improves the collapse of the valve structure towards the base at the time of the diastole, particularly at the beginning of the retrograde flow that occurs at the start of the diastole. During the diastole, the valve structure is therefore positioned towards the bottom, having the inner wall of the stent as support and thus closing the pulmonary orifice.

Regarding the stent, it should be said that it is composed of a lattice having appropriate configuration and material so to be expandable from a compressed state in which it occupies a minimum space, so that it can be percutaneously implanted with its valve and transport the valve through the body ducts, to an open state in which it is completely expanded and rigid, so to be anchored to the destination blood vessel, at the same time providing support for the valve and resisting the recoil forces induced thereon by said blood vessel.

The lattice material is preferably a metal material, in particular steel or a possibly a shape memory metal like nitinol, a plastic or polymer or reabsorbable material.

In accordance with one embodiment of the invention, the lattice is made from a material distinguishable from biological tissue, so to be easily visible by means of non-invasive imaging techniques.

Preferably, the lattice is composed of a mesh of crossed longitudinal and transverse elements whose number and size are chosen to give maximum rigidity both when this lattice is expanded and when it is compressed. Preferably, the lattice has an external curvilinear structure and has a concave form.

In addition, the stent can have an inner or external coating of biocompatible material, preferably ePTFE, in order to optimise the seal of the valve and minimise the reflux in diastole phase.

In accordance with a preferred embodiment of the invention, the stent is made so to have a flaring at the proximal and/or distal end in order to improve the stability of its position.

In the valve prosthesis according to the invention, the valve is made of biocompatible synthetic tissue, material such as Teflon, Dacron, ePTFE, acellular polymers, bio-engineered tissues, polyurethane, scaffolds of various structure. It can also be made biological material such as porcine/equine/bovine pericardium, or other biological material. These materials are widely used in heart surgery and are suitable for resisting in particular the movements that are produced during systoles and diastoles.

According to one aspect of the present invention, the valve is connected along at least one significant portion or zone of the expandable lattice composing the stent, by means of affixing continuous or separate points through positioning of glue, or by means of other fixing systems, such as moulding. These systems permit a suitable fixing of the valve to the stent, thus preventing significant refluxes.

Preferably, in such significant portion or zone, the valve is connected to the stent along at least two junction lines extended in the longitudinal direction of the stent and forming an acute angle with each other. According to a particularly preferred embodiment of the invention, in such significant portion or zone, the valve is connected to the stent along two junction lines, essentially V-shaped, extended in the longitudinal direction of the stent.

An important aspect of the present invention is represented by the positioning of the valve prosthesis in the destination blood vessel, in particular at the pulmonary trunk level. At the time of implantation, the operator evaluates the exact position of the pulmonary branches and right ventricle by examining the image produced by a pulmonary artery and right ventricle angiography with contrast medium. The image is fixed in the same projection and permits evaluating the origin level of the pulmonary branches.

Then, the stent of the valve prosthesis is compressed around a known angioplasty balloon. If the lattice composing the stent is built in its expanded configuration, it will be compressed after the bond of the valve structure by exerting a circular force over its entire periphery, until the smallest compressed configuration is obtained. Advantageously, the lattice composing the stent is visible along the positioning steps of the valve prosthesis, for example by means of fluoroscope.

At this point, the stent with the respective valve and angioplasty balloon are percutaneously inserted in the human body, for example using a femoral vein tract, and are transported to the application point, in particular in the pulmonary trunk zone. Then, the stent is positioned by taking into account the distance between the right ventricle and the pulmonary artery bifurcation. Then, a dilation is carried out with the anglioplasty balloon which permits enlarging the stent, positioning it in the desired point.

The dilation of the balloon can be carried out in a conventional manner, for example by means of inserting a saline solution with contrast means or by coupling the balloon to external inflation means.

When the frame is fully expanded, its structures push on the native tissue. This advantageously produces a penetration of the stent into the wall of the native tissue, permits a stronger fixation to such tissue and reduces the risks of embolism.

As mentioned above, the lattice of the stent is rigid, so to be able to resist the recoil force of the native tissue. Preferably, it does not have flexibility capacity, i.e. when the lattice of the stent has reached its maximum expansion form, it is substantially unchanged without change of size and without change of form. The lattice elements and their number are calculated so to give both maximum rigidity when the lattice is fully expanded, as well as minimum volume when the lattice is in its compressed position.

In accordance with one embodiment of the invention, the angioplasty balloon can be achieved so to have a so-called, "dog bone" form, i.e. that the balloon comprises a central portion having a longitudinal extension substantially equal to that of a corresponding central portion of the stent internally occupied by the valve, and two opposite peripheral portions wider than the central portion, so to flare the stent at opposite ends during the inflation of the balloon.

In such a manner, the fixing of the valve prosthesis is facilitated and the risk of a malpositioning thereof and/or embolisation is reduced or annulled.

Preferably, the end portion of the stent that is subjected to flaring is not affected by the valve, i.e. it does not have insertion points of the valve and preferably corresponds to a line of longitudinal elements of the stent lattice.

Preferably, the size of the dilation of the end portion or portions of the stent subjected to flaring is equal to about 20% more than the diameter of the stent portion affected by the valve.

Another aspect of the present invention regards a method for making a valve prosthesis of the aforesaid type. Such method is characterised in that it comprises the steps of:

providing a stent of material expandable from a compressed state to an entirely expanded state, making a valve in biocompatible synthetic material or providing a biological material valve, coupling said valve in at least one pre-established zone of said stent in its entirely expanded state, so that the valve can be deformed between a closed state in which said valve is entirely spread out in the stent, thus blocking the passage a body flow, and an open state in which said valve, due to the pressure of said body flow, is substantially collapsed on an inner wall of said stent, thus permitting the flow of said body fluid.

Preferably, in said pre-established zone, the valve is connected to the stent along at least two junction lines extended in the longitudinal direction of the stent and forming an acute angle with each other.

According to a particularly preferred mode, in the method of the invention the valve is connected to the stent, at said pre-established zone, along two junction lines, essentially V-shaped, extended in the longitudinal direction of the stent.

Still preferably, in the method according to the invention, the valve is coupled to the stent by means of application of a plurality of suture points along two junction lines extended in the longitudinal direction between the apex and the base of said monocusp sail-like form, said suture points binding the valve to corresponding longitudinal or transverse elements of the lattice composing the stent and/or at intersections between said longitudinal and transverse elements.

The characteristics and advantages of the prosthesis according to the present invention and related achievement method will be clearer from the following description of preferred embodiments, given as indicative and non-limiting with reference to the attached drawings.

DETAILED DESCRIPTION OF PREFERRED EMBODIMENTS OF THE INVENTION

With reference to FIGS. 1-4, a valve prosthesis according to a first embodiment is indicated with 1 in its entirety. The prosthesis 1 is intended to be implanted in body ducts provided with native valves, such as veins or organs, in particular in substitution of native pulmonary valves.

Figure 1:
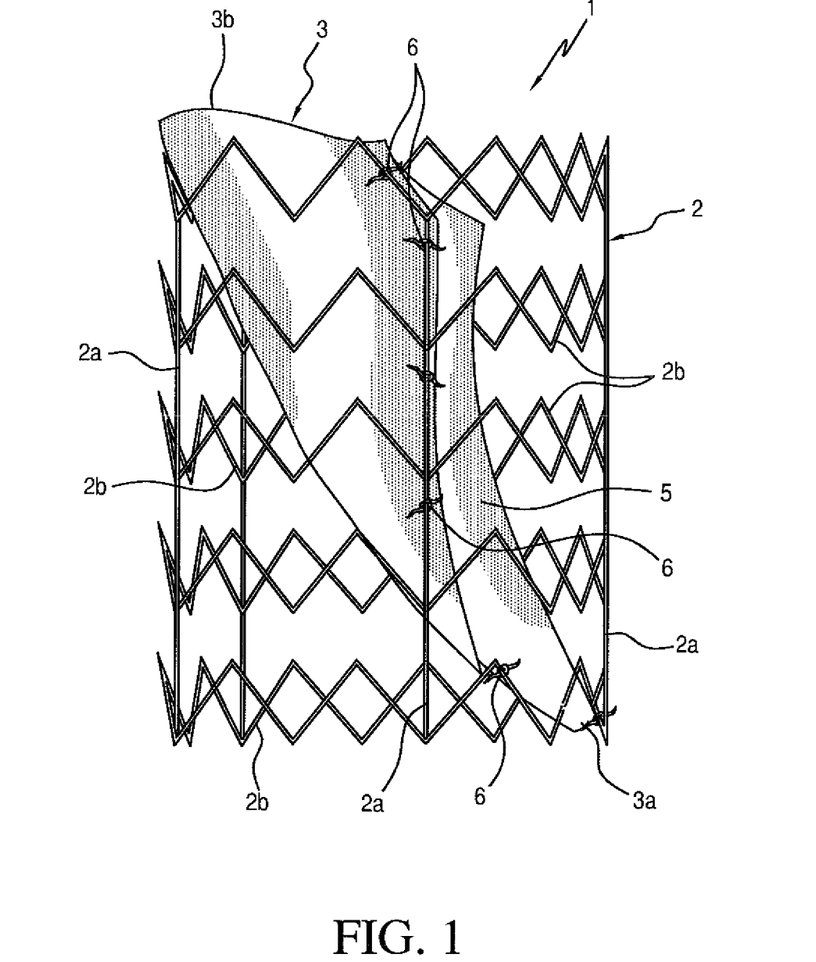
FIG. 1 shows a schematic perspective view of a valve prosthesis according to a first embodiment of the invention.

The valve prosthesis 1 comprises a stent 2 composed of a tubular lattice and a valve 3 arranged inside said stent 2.

Figure 4:
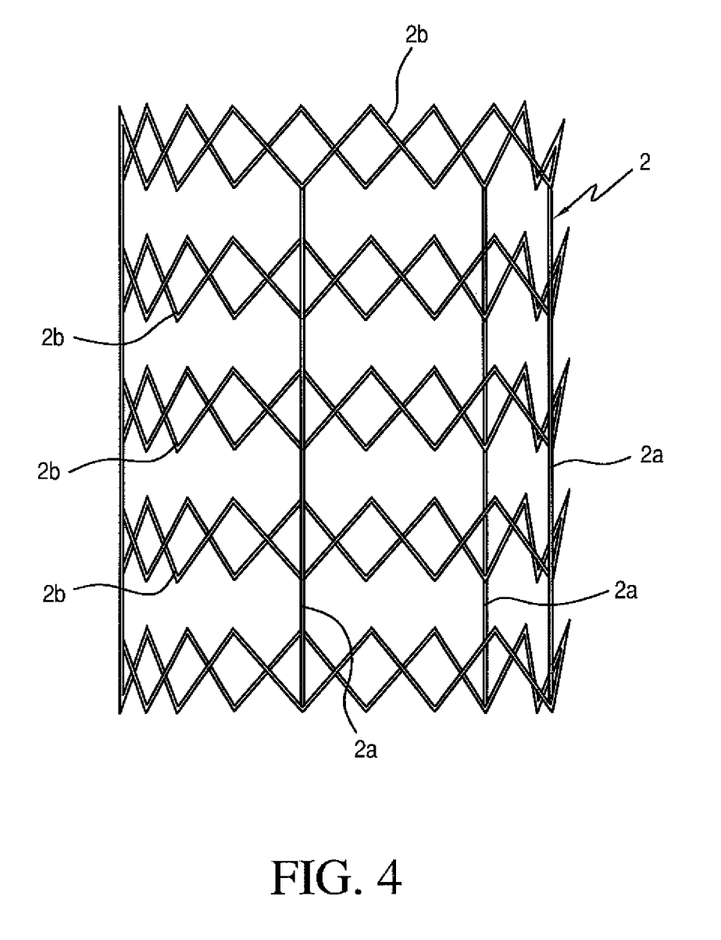
FIG. 4 shows a schematic and perspective view of the stent of the valve prosthesis of FIG. 1.

In particular, the lattice composing the stent 2 comprises longitudinal elements 2a and transverse elements 2b that intersect each other. In the present embodiment, the longitudinal elements 2a are essentially rectilinear, while the transverse elements 2b have a substantially zigzag extension.

The valve 3 is inserted in the stent 2 and has a structure with substantially monocusp sail-like form with substantially triangular longitudinal section and with rounded corners. In particular, the valve 3 has an apex 3a and an opposite base 3b that in use is positioned towards the distal part (pulmonary branches).

Moreover, the valve 3 has a curvature 5 of its surface with concavity turned towards the base 3b, i.e. in use towards the distal part.

In the present embodiment, the monocusp sail-like valve 3 is formed of biocompatible synthetic material, preferably in ePTFE, which is a sufficiently flexible material but is advantageously resistant.

Preferable, the monocusp valve 3 is formed by a sheet of thickness in the range of 0.08-1.12 mm, which is a size compatible with the human body.

In accordance with the present invention, the valve 3 is bound to the stent 2 in pre-established points, so that it can be deformed between a closed state (visible in FIG. 2) in which said valve 3 is fully spread out in the stent 2, thus blocking the passage of a body fluid, and an open state (FIG. 3) in which said valve 3, due to the pressure of said body fluid, is substantially collapsed on an inner wall of said stent 2, thus permitting the flow of said of said body fluid.

In the present embodiment, the bond between the stent 2 and the valve 3 is obtained by means of application of a plurality of suture points 6 in one zone 8 of the stent 2, in particular along two opposite strips longitudinally extended between the apex 3a and the base 3b which bind the valve to corresponding longitudinal elements 2a or transverse elements 2b of the lattice composing the stent 2.

In addition, the valve 3 is bound to the stent 2 so to be arranged, in its open state, tilted with reference to the longitudinal axis of the stent by an acute angle with respect to such axis preferably in the range of 35-50°, and in a particularly preferred measurement, about 45°.

Figure 5:
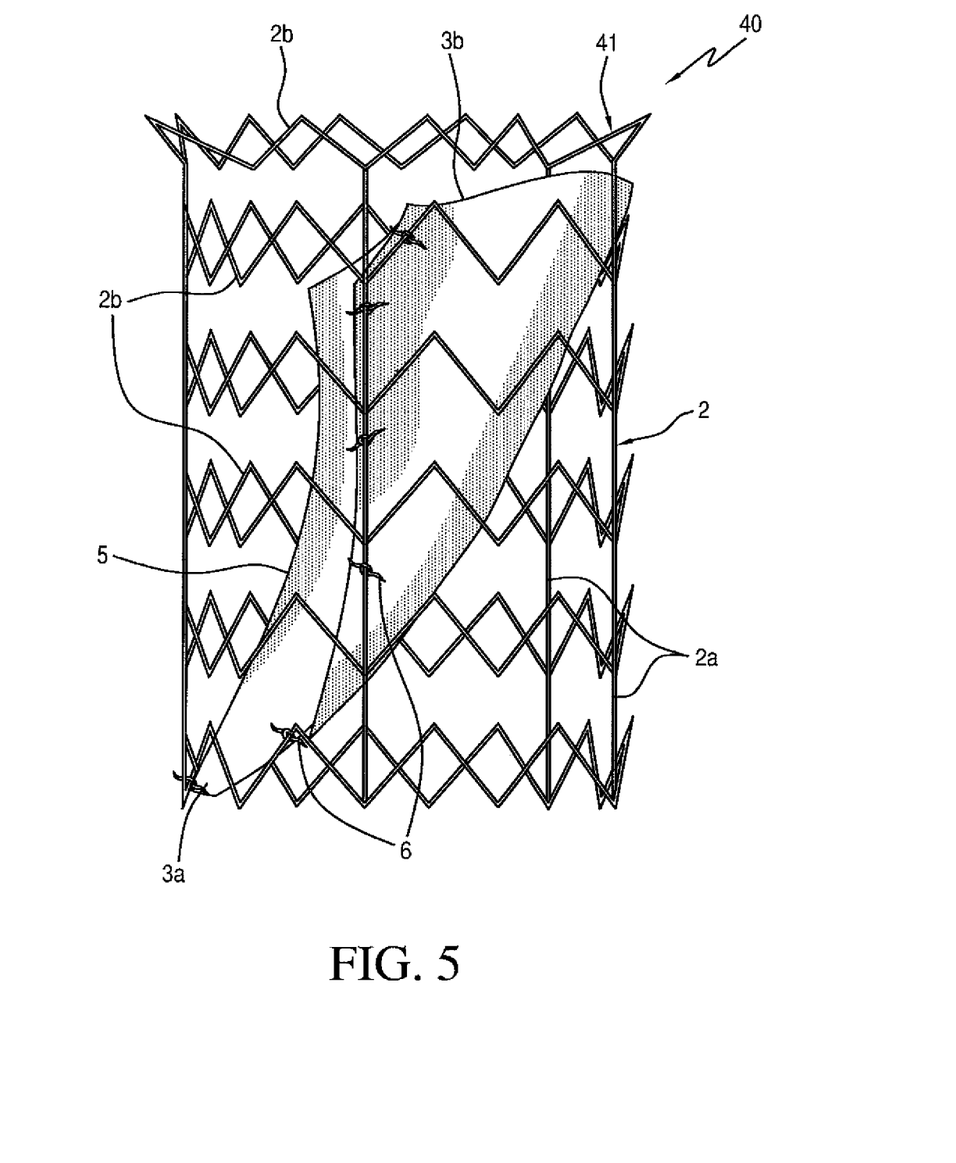
FIG. 5 shows a schematic perspective view of a valve prosthesis according to a second embodiment of the invention.
Figure 6:
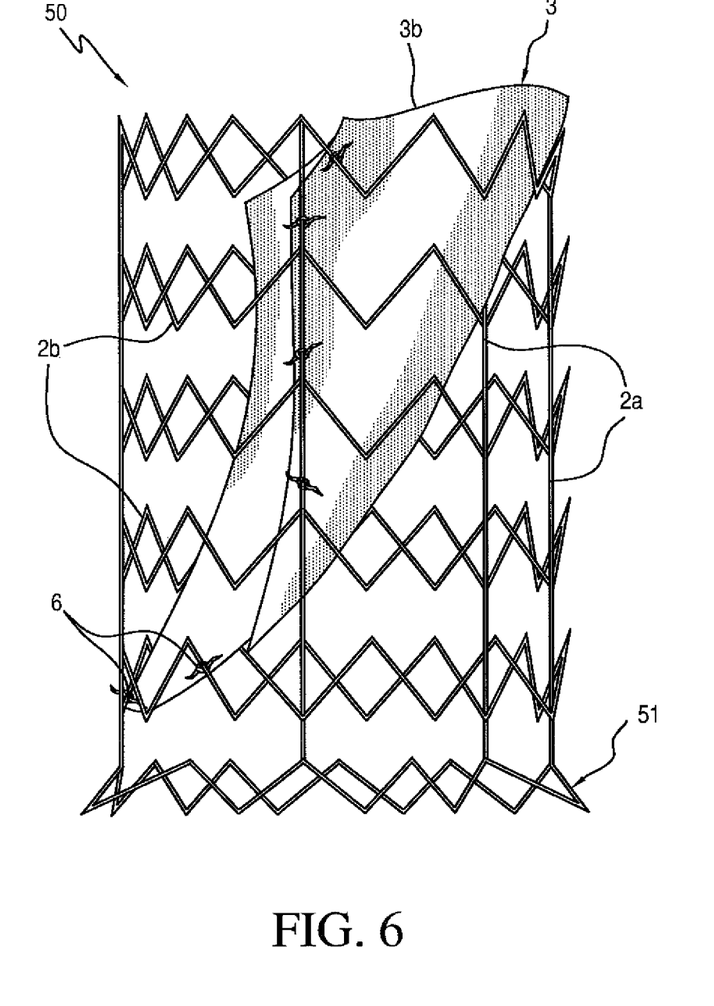
FIG. 6 shows a schematic perspective view of a valve prosthesis according to a third embodiment of the invention.
Figure 7:
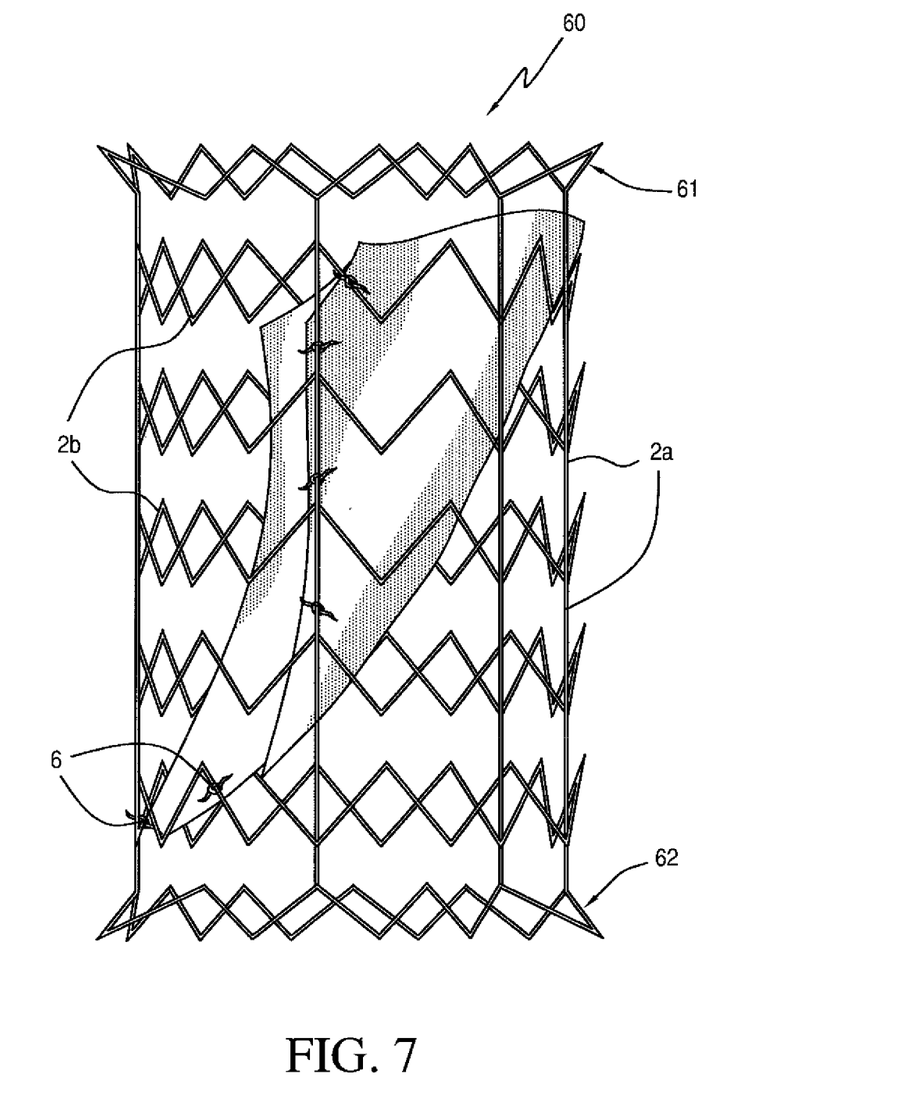
FIG. 7 shows a schematic perspective view of a valve prosthesis according to a fourth embodiment of the invention.

In FIGS. 5-7, valve prostheses are shown in accordance with further embodiments of the invention, in which the same reference numbers are attributed to elements structurally or functionally equivalent to corresponding elements of the valve prosthesis 1 described above.

In particular, in FIG. 5, a valve prosthesis is shown that is indicated in its entirety with 40, which differs from the prosthesis 1 described above since an end portion 41 of the stent 2 (in the specific case the distal end) is flared, so to improve the anchoring of the prosthesis 40 in the application site and to avoid refluxes.

In FIG. 6, on the other hand, it is shown a valve prosthesis indicated in its entirety with 50 which differs from the prosthesis 1 described above in that an end portion 51 of the stent 2 (in the specific case, the proximal end) is flared, so to improve the anchoring of the prosthesis 50 in the site of application.

In FIG. 7, on the other hand, a valve prosthesis is indicated in its entirety with 60 which differs from the prosthesis 1 described above in that two opposite end portions, 61 and 62, respectively, of the stent 2 are both flared, so to improve the anchoring of the prosthesis 60 in the site of application.

Figure 2:
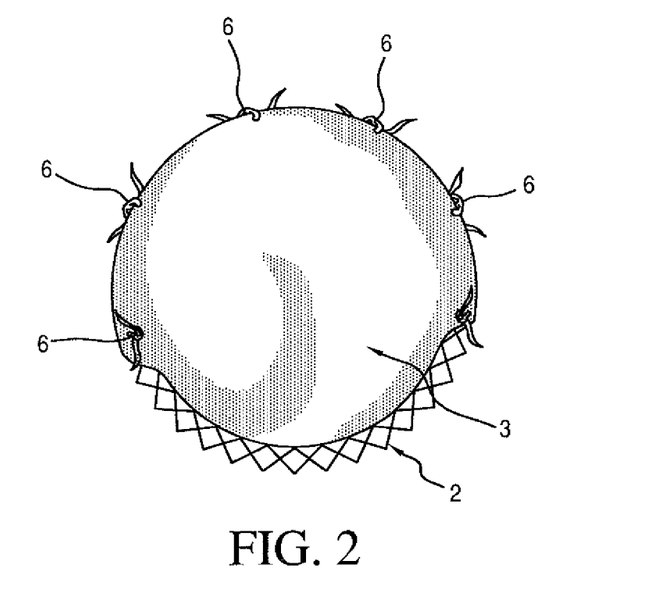
FIG. 2 shows a schematic top view of the valve prosthesis of FIG. 1 in its closed position.
Figure 3:
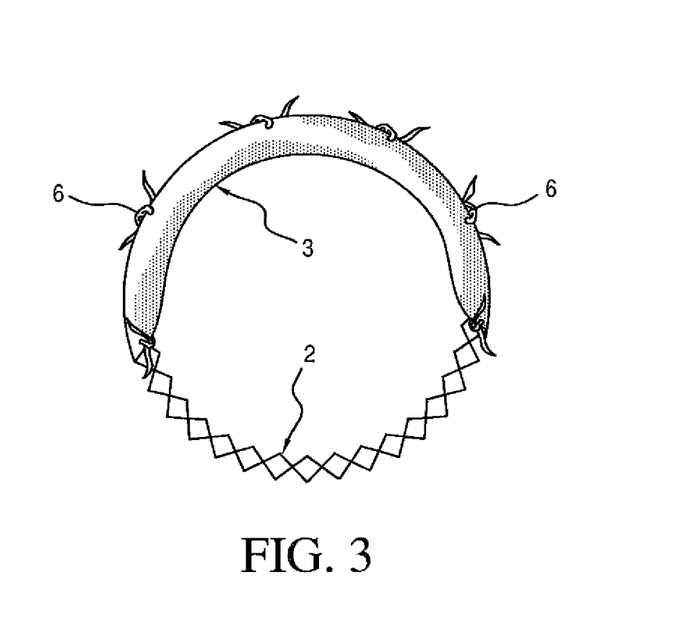
FIG. 3 shows a schematic top view of the valve prosthesis of FIG. 1 in its open position.
Figure 8:
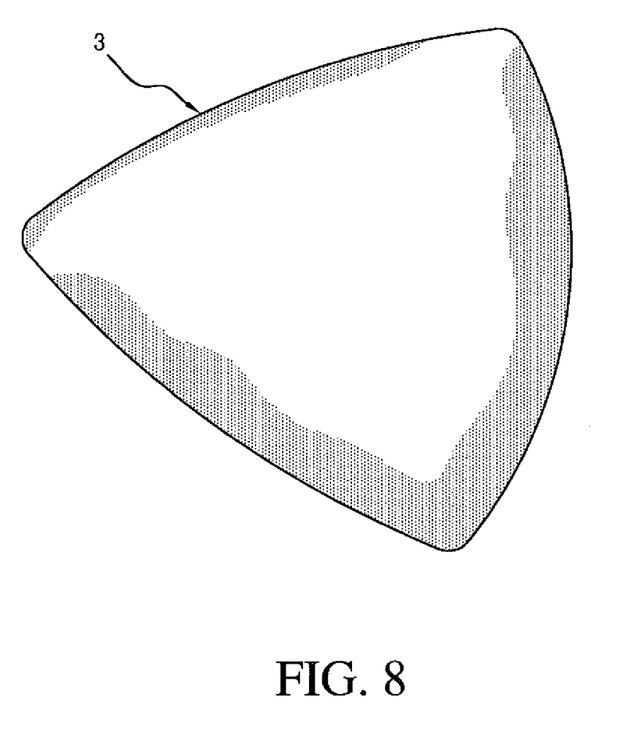
FIGS. 8 and 9 illustrate respective steps of the achievement method of a valve prosthesis according to the invention, and
FIGS. 10 and 11 schematically show a valve prosthesis of the invention, respectively with or without stent coating, inserted at the pulmonary trunk level.
Figure 9:
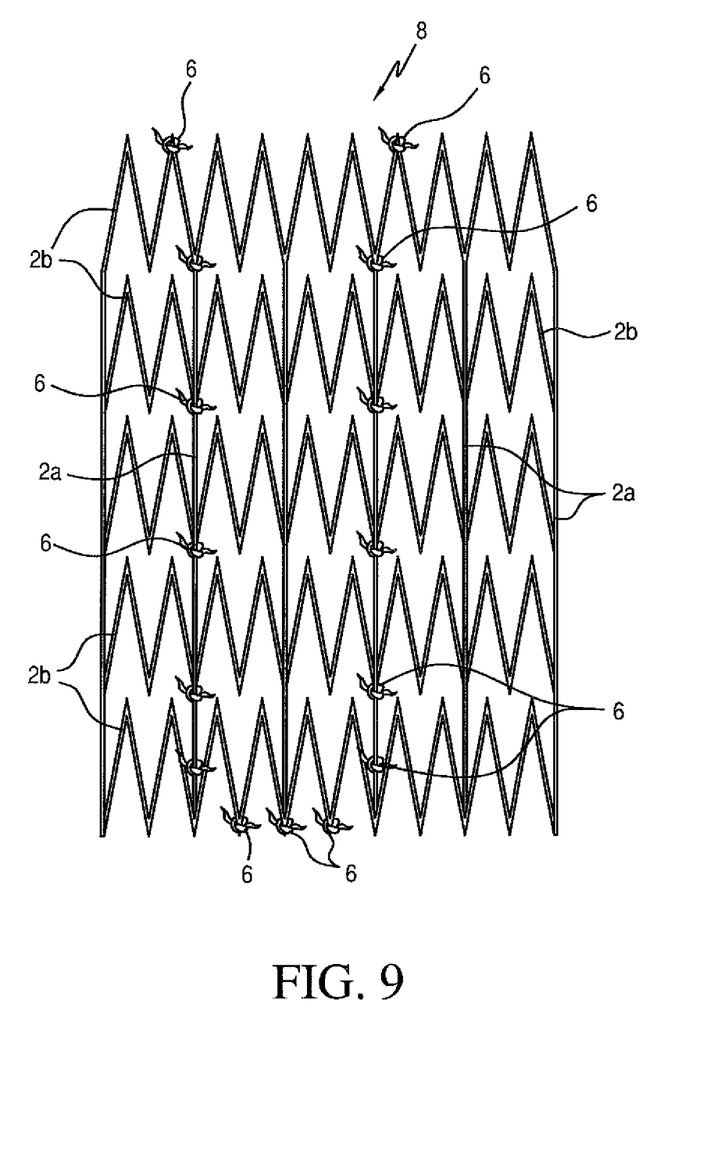

FIGS. 8 and 9 illustrate several steps of the achievement method of a valve prosthesis according to the invention, for example of the valve prosthesis 1 of FIGS. 1-3.

Having a stent 2 available (or previously manufactured), the first step is that of creating the valve 3 from a rectangular sheet of the chosen material, preferably ePTFE. The ratio between the length of the sheet from which one obtains the valve 3 is preferably equal to about 1.3-1.5 times the length of the stent 2. The ratio between the width of the sheet from which one obtains the valve 3 is preferably equal to about 1.5-1.7 times the width of the stent 2.

In the lower and upper parts, the quadrangular sheet is cut in a manner so as to obtain a triangular sail-like form with rounded sides (FIG. 8).

Subsequently, one proceeds with binding the monocusp valve 3 to the stent 2 in a predetermined zone 8 along two junction lines, preferably forming a V from the proximal side to the distal side. Such operation is shown in FIG. 9 by means of suture points preferably placed at the intersections between the longitudinal elements 2a and the transverse elements 2b delimiting a longitudinal zone 8 of the stent 2. In particular, starting from the proximal position closest to the ventricle (end on the bottom of FIG. 9), three points are positioned along the base row starting from the central longitudinal element 2a of the zone 8 of the stent 2, then an intermediate point is positioned on the two longitudinal elements 2a contiguous to said central longitudinal element 2a in an intermediate position between the first transverse element 2b and the second transverse element 2b (moving from the bottom upward). Subsequently, five points are placed (but a lower number could also be placed, such as three or four) along the aforesaid longitudinal elements 2a contiguous with the central longitudinal element 2a at the intersections with respective lines of transverse elements 2b of the stent 2. Thus, in the present preferred embodiment, in a stent with five longitudinal elements, the valve is positioned by occupying two elements with points affixed in a zone 8 of the stent 2 along two V-shaped junction lines, preferably along the entire length of the stent 2 in addition to the base line.

The coupling of the valve 3 to the stent 2 is carried out with the stent in fully expanded state. Once the valve 3 is bound, the stent 2 can be recompressed in a manner such to permits percutaneous insertion in the human body, for example in the femoral vein vessel. An introducer of about 12 French is normally sufficient for the insertion of the valve prosthesis according to the invention that, once implanted, is capable of lasting at least 10 years without defects.

In order to prevent the risks of thrombus formations, one uses compatible material already used in heart surgery for many years. The valve structure can ideally have different forms and designs, composed of a triangular form with rounded sides. A sail-like structure can be reinforced by means of rectilinear or tilted points, in order to avoid that it curls up on itself.

Figure 10:
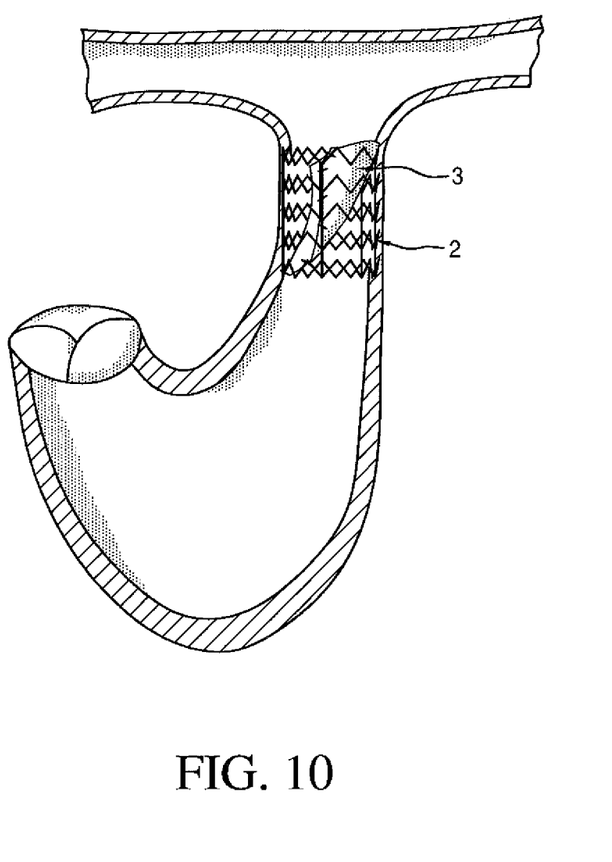
Figure 11:
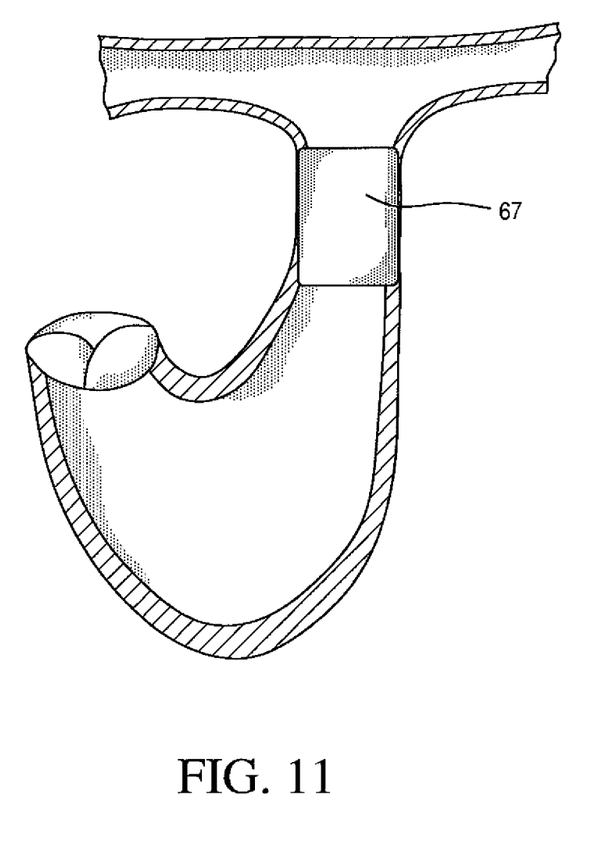

FIGS. 10 and 11 schematically show a valve prosthesis according to the invention inserted at pulmonary trunk level, with the stent in totally expanded state.

It is noted in particular that the valve prosthesis according to the invention is inserted in the pulmonary trunk and can have a flared aspect (not shown) in order to improve the seal on the pulmonary side and minimise the risks of embolisation.

In addition, as shown in FIG. 11, the stent 2 of the valve prosthesis according to the invention is externally coated (but it could also be internally coated, or both internally and externally coated) with a layer 67 of biocompatible material, preferably ePTFE. Such coating is, on the other hand, absent in the valve prosthesis implanted at the pulmonary trunk level shown in FIG. 10.

Regarding the configurations of the stent of the valve prosthesis according to the invention, it is useful to specify that a cylindrical stent 2 in the compressed state preferably has a diameter of 3-4 mm in order to reach a diameter of 23-28 mm in the maximum expansion state. As said above, the stent 2 can have different configurations in accordance with the number of longitudinal and transverse elements composing the lattice, as well as the number of intersections between said elements. This number, as with the size and force of the lines, is calculated in a manner such to permits the passage of the structure from 3-4 mm to a diameter of 23-28 mm.

Preferably, the length of the stent in the fully dilated state (i.e. in the maximum expansion state) is 30-50 mm.

The main advantage of the prosthesis valve according to the invention lies in its applicability to the valve pathologies in general and pulmonary pathologies in particular, permitting the reparation of a valve defect with a minimally-invasive technique that substitutes the surgery, avoiding sternotomy and extracorporeal circulation.

In particular, the valve prosthesis according to the invention is readily applicable to pluri-operated subjects in whom a further surgical operation would be a too high risk.

Another advantage of the valve prosthesis according to the invention lies in the high effectiveness of the valve which is capable of regulating the flow of body fluid, in particular blood, in harmony with the cardiac cycle. To this end, it should be noted that in the open state, the valve is advantageously collapsed entirely on the inner wall of the stent, thus permitting a high cross section for the passage of the body fluid (for example blood), such cross section being slightly less than that of the stent.

A further advantage of the prosthesis according to the invention lies in the fact that it can be implanted inside the human body with ease and in a minimally invasive manner, due to the fact that the stent can be reduced to very small sizes in the compressed state, thus facilitating the percutaneous insertion.

Finally, the last advantage, but of no less importance than the others, lies in the high resistance of the stent to the recoil forces induced by the blood vessel in which the valve prosthesis is applied, which permits maintaining a high flow section for the body fluid. Moreover, the presence of flaring at the end or at the ends of the stent improves the anchoring of the valve prosthesis.

A man skilled in the art can make numerous modifications and variants to the valve prosthesis and related method of making described above, all moreover comprised in the scope of protection of the attached claims.

The invention claimed is:

1. A cardiac valve prosthesis comprising:
   a stent, which is cylindrical and expandable from a compressed state for percutaneous implantation, to an expanded state for anchoring to a vessel, said stent including a distal end and a proximal end located at terminal ends of said stent, and formed from a plurality of longitudinal rectilinear elements abutting a plurality of, separate and distinct, crossed transverse elements whereby each of said crossed transverse elements traverse and cross each of said longitudinal rectilinear elements, and each of said longitudinal rectilinear elements extend continuously from said distal end to said proximal end substantially parallel to a longitudinal axis of said stent;
   a plurality of sutures; and
   a triangular cardiac valve having a first side and second side both extending from an apex of said valve to an opposite base of said valve, said valve arranged in said stent and being bound to said stent in a pre-established zone along said longitudinal rectilinear elements and said crossed transverse elements by said sutures at a plurality of suture points along said first side and said second side of said valve thereby binding said valve to said longitudinal rectilinear elements and said crossed transverse elements, wherein said valve is connected to said stent in said pre-established zone along at least two junction lines tracking said first and second sides of said valve whereby said junction lines form an acute angle with each other at a position proximal to said apex of said valve.

2. The cardiac valve prosthesis according to claim 1, wherein said valve in said expanded state has a substantially triangular longitudinal section and rounded corners.

3. The cardiac valve prosthesis according to claim 2, wherein said valve has a curvature of a concave surface as said valve extends from said apex to said base.

4. The cardiac valve prosthesis according to claim 2, wherein said valve in said expanded state exhibits a slope at an angle of 35-50° with reference to a longitudinal axis of said stent.

5. The cardiac valve prosthesis according to claim 4, wherein said valve exhibits said slope with reference to the longitudinal axis of said stent of about 45°.

6. The cardiac valve prosthesis according to claim 1, wherein said valve is made of a biocompatible synthetic material.

7. The cardiac valve prosthesis according to claim 6, wherein said material is ePTFE.

8. The cardiac valve prosthesis according to claim 1, wherein said stent is made of a metal or plastic material.

9. The cardiac valve prosthesis according to claim 1, wherein said stent has an inner coating, an outer coating, or both said inner coating and said outer coating of biocompatible material.

10. The cardiac valve prosthesis according to claim 1, wherein said stent has a flaring at said proximal end, at said distal end, or at both said proximal end and said distal end.

11. The cardiac valve prosthesis according to claim 1, wherein said stent has an inner or outer coating of ePTFE.

12. The cardiac valve prosthesis according to claim 1, wherein said crossed transverse elements extend substantially perpendicular to said longitudinal rectilinear elements.

13. The cardiac valve prosthesis according to claim 12, wherein said crossed transverse elements extend in a zig-zag manner.

14. A method for making a cardiac valve prosthesis according to claim 1, wherein the method comprises the steps of:
   providing a stent of material expandable from a compressed state to a fully expanded state, said stent including a distal end and a proximal end located at terminal ends of said stent, and formed from a plurality of longitudinal rectilinear elements abutting a plurality of, separate and distinct, crossed transverse elements whereby each of said crossed transverse elements traverse and cross each of said longitudinal rectilinear elements, and each of said longitudinal rectilinear elements extend continuously from said distal end to said proximal end substantially parallel to a longitudinal axis of said stent;
   providing a triangular cardiac valve of biocompatible or biological material, said valve having a first side and a second side both extending from an apex of said valve to an opposite base of said valve; and
   suturing said valve to said stent in a pre-established zone along said longitudinal rectilinear elements and said crossed transverse elements at a plurality of suture points along said first side and said second side of said valve thereby binding said valve to said longitudinal rectilinear elements and said crossed transverse elements, wherein said valve is connected to said stent in said pre-established zone along two junction lines tracking said first and second sides of said valve whereby said junction lines form an acute angle with each other at a position proximal to said apex of said valve.

15. The method according to claim 14, wherein said valve is made from a sheet of thickness in the range of 0.08 mm-1.12 mm.

16. The method according to claim 14, wherein said crossed transverse elements extend substantially perpendicular to said longitudinal rectilinear elements.

17. The method according to claim 16, wherein said crossed transverse elements extend in a zig-zag manner.

* * * * *